United States Patent
Laffitte et al.

(10) Patent No.: US 11,344,540 B2
(45) Date of Patent: May 31, 2022

(54) METHODS FOR TREATING LIVER DISORDERS USING FXR AGONISTS

(71) Applicant: Novartis AG, Basel (CH)

(72) Inventors: Bryan Laffitte, San Diego, CA (US); Michael Badman, Cambridge, MA (US); Jin Chen, East Hanover, NJ (US); Sam Lindgren, Basel (CH)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 16/078,409

(22) PCT Filed: Feb. 20, 2017

(86) PCT No.: PCT/IB2017/050963
§ 371 (c)(1),
(2) Date: Aug. 21, 2018

(87) PCT Pub. No.: WO2017/145041
PCT Pub. Date: Aug. 31, 2017

(65) Prior Publication Data
US 2019/0046519 A1    Feb. 14, 2019

Related U.S. Application Data (60) Provisional application No. 62/420,661, filed on Dec. 12, 2016, provisional application No. 62/298,121, filed on Feb. 22, 2016.

(51) Int. Cl.
| | |
|---|---|
| *A61K 31/46* | (2006.01) |
| *A61P 1/12* | (2006.01) |
| *A61K 31/506* | (2006.01) |
| *A61K 31/497* | (2006.01) |
| *A61K 31/4748* | (2006.01) |
| *A61K 47/54* | (2017.01) |
| *A61P 1/16* | (2006.01) |
| *A61K 9/00* | (2006.01) |

(52) U.S. Cl.
CPC ............ *A61K 31/46* (2013.01); *A61K 9/0053* (2013.01); *A61K 31/4748* (2013.01); *A61K 31/497* (2013.01); *A61K 31/506* (2013.01); *A61K 47/542* (2017.08); *A61P 1/16* (2018.01)

(58) Field of Classification Search
CPC ....... A61K 31/46; A61K 31/4758; A61P 1/00; A61P 1/16
See application file for complete search history.

(56) References Cited

U.S. PATENT DOCUMENTS

| | | |
|---|---|---|
| 2019/0046518 A1 | 2/2019 | Laffitte et al. |
| 2019/0083481 A1 | 3/2019 | Laffitte et al. |

FOREIGN PATENT DOCUMENTS

| | | |
|---|---|---|
| CL | 2016000982 A1 | 10/2016 |
| JP | 2019-511476 A | 4/2019 |
| WO | WO2012087519 A1 | 6/2012 |
| WO | 2015124727 A1 | 8/2015 |
| WO | 2017/145040 A1 | 8/2017 |

OTHER PUBLICATIONS

Genin et al. Discovery of 6-(2-{[5-cyclopropyl-3-(2,6-dichlorophenyl)isoxazol-4-yl]methoxy}piperidin-1-yl)-1-methyl-1H-indole-3-carboxylic acid: a novel FXR agonist for the treatment of dyslipidemia. J. Med. Chem. 2015, 58, 9768-9772. Published online Nov. 14, 2015.*
Carr. FXR agonsits as therapeutic agents for non-alcoholic fatty aliver disease. Curr. Atheroscler. Rep. 2015, 17:16.*
Cariou. The farnesoid X receptor (FXR) as a new target in non-alcoholic steatohepatitis. Diabetes & Metabolism, 34, 2008, 685-691.*
Cheng et al. Chronic activation of FXR in transgenic mice caused perinatal toxicity and sensitized mice to cholesterol toxicity. (Molecular Endocrinology, 29: 571-582, 2015).*
Jung et al., "FXR agonists and FGF15 reduce fecal bile acid excretion in a mouse model of bile acid malabsorption", Journal of Lipid Research, vol. 48, No. 12, pp. 2693-2700, Aug. 25, 2007.
U.S. Appl. No. 16/078,431 (2019-0083481).
U.S. Appl. No. 16/078,403 (2019-0046518).
Regan et al., "Acyl Glucuronides:The Good, The Bad and the Ugly," Biopharmaceutics & Drug Disposition, Sep. 9, 2010, pp. 367-395, 31, DOI: 10.1002/bdd.720.

* cited by examiner

*Primary Examiner* — Theodore R. Howell
(74) *Attorney, Agent, or Firm* — Emily T. Wu (57) ABSTRACT

The invention provides methods for modulating the activity of farnesoid X receptors (FXRs) using specific FXR agonists, in particular for treating or preventing liver diseases.

25 Claims, 2 Drawing Sheets

METHODS FOR TREATING LIVER DISORDERS USING FXR AGONISTS

FIELD OF THE INVENTION

The present invention relates to novel regimens for treating or preventing liver conditions mediated by farnesoid X receptors (FXRs), by using therapeutically effective amount of a FXR agonist, as well as methods, uses, compositions involving such regimens.

BACKGROUND OF THE INVENTION

Farnesoid X Receptor Agonist (FXR) is a nuclear receptor activated by bile acids, also known as Bile acid Receptor (BAR). FXR is expressed in principal sites of bile acid metabolism, such as liver, intestine and kidney, where it mediates effects on multiple metabolic pathways in a tissue-specific manner.

The mode of action of FXR in the liver and intestine is well known, and described e.g. in (Calkin and Tontonoz, (2012), Nature Reviews Molecular Cell Biology 13, 213-24). FXR is responsible for modulating bile acid production, conjugation and elimination through multiple mechanisms in the liver and intestine. In normal physiology, FXR detects increased levels of bile acids and responds by decreasing bile acid synthesis and bile acid uptake while increasing bile acid modification and secretion in the liver. In the intestine, FXR detects increased bile acid levels and decreases bile acid absorption and increases secretion of FGF15/19. The net result is a decrease in the overall levels of bile acids. In the liver, FXR agonism increases expression of genes involved in canalicular and basolateral bile acid efflux and bile acid detoxifying enzymes while inhibiting basolateral bile acid uptake by hepatocytes and inhibiting bile acid synthesis.

Furthermore, FXR agonists decrease hepatic triglyceride synthesis leading to reduced steatosis, inhibit hepatic stellate cell activation reducing liver fibrosis and stimulate FGF15/FGF19 expression (a key regulator of bile acid metabolism) leading to improved hepatic insulin sensitivity. Thus, FXR acts as a sensor of elevated bile acids and initiates homeostatic responses to control bile acid levels, a feedback mechanism that is believed to be impaired in cholestasis. FXR agonism has shown clinical benefits in subjects with cholestatic disorders (Nevens et al., J. Hepatol. 60 (1 SUPPL. 1): 347A-348A (2014)), bile acid malabsorption diarrhea (Walters et al., Aliment Pharmacol. Ther. 41(1):54-64 (2014)) and non-alcoholic steatohepatitis (NASH; Neuschwander-Tetri et al 2015).

Bile acids are normally produced by the organism. At high dose they can cause different side effects as they have detergent properties (diarrhea or cellular injury). In addition they can also cause pruritus.

Obeticholic acid (6α-ethyl-chenodeoxycholic acid), that is abbreviated to OCA and also known as INT-747, is a bile acid-derived FXR agonist, analogue to the natural bile acid chenodeoxycholic acid. In clinical studies, OCA showed efficacy in both Primary Biliary Cirrhosis (PBC) and non-alcoholic steatohepatitis (NASH) subjects; however OCA treatment may be associated with increased pruritus. OCA was tested at doses between 5 mg and 50 mg in PBC subjects or NASH subjects.

There remains a need for new treatments and therapies for liver conditions mediated by FXR, which could be associated with more limited side effects.

SUMMARY OF THE INVENTION

The invention provides methods of treating, preventing, or ameliorating conditions mediated by farnesoid X receptors (FXR), in particular liver diseases, comprising administering to a subject in need thereof a therapeutically effective amount of a FXR agonist of formula (I)

(I)

(i.e. 2-[3-({5-cyclopropyl-3-[2-(trifluoromethoxy)phenyl]-1,2-oxazol-4-yl}methoxy)-8-azabicyclo[3.2.1]octan-8-yl]-4-fluoro-1,3-benzothiazole-6-carboxylic acid), a stereoisomer, an enantiomer, a pharmaceutically acceptable salt or an amino acid conjugate thereof, e.g. a FXR agonist of formula (II)

(II)

(i.e. 2-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]-4-fluoro-1,3-benzothiazole-6-carboxylic acid) (as herein defined as Compound A), in free form, or a pharmaceutically acceptable salt or an amino acid conjugate thereof, e.g. a FXR agonist of formula (III)

(III)

(i.e. 2-({2-[(1R,3R,5S)-3-({5-cyclopropyl-3-[2-(trifluoromethoxy)phenyl]-1,2-oxazol-4-yl}methoxy)-8-azabicyclo[3.2.1]octan-8-yl]-4-fluoro-1,3-benzothiazol-6-yl}formamido)acetic acid) (Compound B),
of formula (IV)

(i.e. 2-({2-[(1R,3R,5S)-3-({5-cyclopropyl-3-[2-(trifluoromethoxy)phenyl]-1,2-oxazol-4-yl}methoxy)-8-azabicyclo[3.2.1]octan-8-yl]-4-fluoro-1,3-benzothiazol-6-yl}formamido)ethane-1-sulfonic acid) (Compound C),
of formula (V)

(i.e. 2S,3S,4S,5R,6S)-6-((2-((1R,3S,5S)-3-((5-cyclopropyl-3-(2-(trifluoromethoxy)phenyl)isoxazol-4-yl)methoxy)-8-azabicyclo[3.2.1]octan-8-yl)-4-fluorobenzo[d]thiazole-6-carbonyl)oxy)-3,4,5-trihydroxytetrahydro-2H-pyran-2-carboxylic acid (Compound D), or a pharmaceutically acceptable salt thereof.

The invention further provides new dosing regimens of FXR agonists of formula (I), a stereoisomer, an enantiomer, a pharmaceutically acceptable salt or an amino acid conjugate thereof, e.g. Compound A or amino acid conjugate thereof, e.g. glycine conjugate, taurine conjugate or acyl glucuronide conjugate of Compound A, e.g. Compound A, for treating or preventing liver diseases and disorders mediated by farnesoid X receptors (FXR), as well as the use of such new regimens and pharmaceutical compositions adapted for administering such new regimens. Such new dosing regimens are effective and well tolerated regimens for treating or preventing liver diseases and disorders mediated by farnesoid X receptors (FXR) in humans.

In comparison to OCA, the non-bile acid FXR agonists disclosed herein, e.g. Compound A is ~300× more potent, with no FGR5 effects therefore has a greater specificity when administered to a patient in need thereof.

The compounds of formula (I) (e.g. Compound A) are non-bile acid derived FXR agonists. They are described in WO2012/087519.

Non-bile acid derived FXR agonists have the advantages of greater potency, greater specificity for the FXR target and absorption, distribution, metabolism and elimination processes that are not subject to processes of bile acid metabolism.

Various (enumerated) embodiments of the disclosure are described herein. It will be recognized that features specified in each embodiment may be combined with other specified features to provide further embodiments of the present disclosure.

Embodiment 1

Therapeutic regimens for treating or preventing a condition mediated by Farnesoid X receptor (FXR), comprising administering the FXR agonist of formula (I), a stereoisomer, an enantiomer, a pharmaceutically acceptable salt thereof or an amino acid conjugate thereof, e.g. Compound A, e.g in free form or an amino acid conjugate thereof, at a dose (e.g. daily dose) of about 3 μg, to about 100 μg, about 5 μg, to about 100 μg, e.g. about 10 μg, to about 100 μg, e.g. about 20 μg, to 100 μg, e.g. about 30 μg, to about 90 μg, e.g. about 40 μg, to about 60 μg; or at a dose in a range of about 10 μg, to about 60 μg, e.g. about 10 μg, to about 40 μg, e.g. about 20 μg, to about 40 μg; or at a dose in a range of about 20 μg, to about 60 μg, e.g. about 30 μg, to about 60 μg; or at a dose in a range of about 5 μg, to about 60 μg, e.g. about 5 μg, to about 40 μg, e.g. about 3 μg, to about 40 μg. e.g. about 3 μg, to about 30 μg. Such doses may be for daily or twice daily administration.

Embodiment 2

Therapeutic regimens for treating or preventing a condition mediated by Farnesoid X receptor (FXR), comprising administering the FXR agonist of formula (I), a stereoisomer, an enantiomer, a pharmaceutically acceptable salt thereof or an amino acid conjugate thereof, e.g. Compound A, e.g in free form or an amino acid conjugate thereof, at a dose of about 3 µg, about 4 µg, about 5 µg, about 10 µg, about 20 µg, about 25 µg, about 30 µg, about 40 µg, about 60 µg, or about 90 µg, or about 120 µg. Such doses may be for daily administration (e.g. daily doses). Such doses may be for twice daily.

Embodiment 3

Therapeutic regimens for treating or preventing a condition mediated by Farnesoid X receptor (FXR) such as a liver or an intestinal disease, comprising administering the FXR agonist of formula (I), a stereoisomer, an enantiomer, a pharmaceutically acceptable salt thereof or an amino acid conjugate thereof, e.g. Compound A or an amino acid conjugate thereof, at a dose of about 10 µg, e.g. daily or twice daily, e.g. for daily administration.

Embodiment 4

Therapeutic regimens for treating or preventing a condition mediated by Farnesoid X receptor (FXR) such as a liver or an intestinal disease, comprising administering the FXR agonist of formula (I), a stereoisomer, an enantiomer, a pharmaceutically acceptable salt thereof or an amino acid conjugate thereof, e.g. Compound A or an amino acid conjugate thereof, at a dose of about 25 µg, or about 30 µg, e.g. daily or twice daily, e.g. for daily administration.

Embodiment 5

Therapeutic regimens for treating or preventing a condition mediated by Farnesoid X receptor (FXR) such as a liver or an intestinal disease, comprising administering the FXR agonist of formula (I), a stereoisomer, an enantiomer, a pharmaceutically acceptable salt thereof or an amino acid conjugate thereof, e.g. Compound A or an amino acid conjugate thereof, at a daily dose of about 60 µg, e.g. daily or twice daily, e.g. for daily administration.

Embodiment 6

Therapeutic regimens for treating or preventing a condition mediated by Farnesoid X receptor (FXR) such as a liver or an intestinal disease, comprising administering the FXR agonist of formula (I), a stereoisomer, an enantiomer, a pharmaceutically acceptable salt thereof or an amino acid conjugate thereof, e.g. Compound A or an amino acid conjugate thereof, at a daily dose of about 90 µg, e.g. daily or twice daily, e.g. for daily administration.

Embodiment 7

Use of a FXR agonist of formula (I), a stereoisomer, an enantiomer, a pharmaceutically acceptable salt thereof or an amino acid conjugate thereof, e.g. Compound A or an amino acid conjugate thereof, in the manufacture of a medicament for treating or preventing a condition mediated by Farnesoid X receptor (FXR), wherein the FXR agonist is to be administered at a dose (e.g. daily dose), of about 3 µg, to about 120 µg, e.g. about 5 µg, to about 120 µg, e.g. about 10 µg, to about 120 µg, e.g. about 20 µg, to 100 µg, e.g. about 30 µg, to about 90 µg, e.g. about 40 µg, to about 60 µg; or at a dose of about 10 µg, to about 60 µg, e.g. about 10 µg, to about 40 µg, e.g. about 20 µg, to about 40 µg; or at a dose of about 20 µg, to about 60 µg, e.g. about 30 µg, to about 60 µg; or at a dose of about 5 µg, to about 60 µg, e.g. about 5 µg, to about 40 µg, e.g. about 3 µg, to about 40 µg. e.g. about 3 µg, to about 30 µg. Such doses may be for administration daily (daily doses) or twice daily, e.g. for daily administration.

Embodiment 8

Use of a FXR agonist of formula (I), a stereoisomer, an enantiomer, a pharmaceutically acceptable salt thereof or an amino acid conjugate thereof, e.g. Compound A or an amino acid conjugate thereof, in the manufacture of a medicament for treating or preventing a condition mediated by Farnesoid X receptor (FXR), wherein the FXR agonist is to be administered at a dose of about 3 µg, about 4 µg, about 5 µg, about 10 µg, about 20 µg, about 25 µg, about 30 µg, about 40 µg, about 60 µg, about 90 µg, or about 120 µg. Such doses may be for daily administration (e.g. daily doses) or daily or twice daily, e.g. for daily administration.

Embodiment 9

Use of a FXR agonist of formula (I), a stereoisomer, an enantiomer, a pharmaceutically acceptable salt thereof or an amino acid conjugate thereof, e.g. Compound A or an amino acid conjugate thereof, in the manufacture of a medicament for treating or preventing a condition mediated by Farnesoid X receptor (FXR), wherein the FXR agonist is to be administered at a dose of about 3 µg/day to about 120 µg/day, about 5 µg/day to about 120 µg/day, e.g. about 10 µg/day to about 100 µg/day, e.g. about 20 µg/day to 100 µg/day, e.g. about 30 µg/day to about 90 µg/day, e.g. about 40 µg/day to about 60 µg/day; or at a dose of about 10 µg/day to about 60 µg/day, e.g. about 10 µg/day to about 40 µg/day, e.g. about 20 µg/day to about 40 µg/day; or at a dose of about 20 µg/day to about 60 µg/day, e.g. about 30 µg/day to about 60 µg/day; or at a dose of about 5 µg/day to about 60 µg/day, e.g. about 5 µg/day to about 40 µg/day; or at a dose of about 3 µg/day to about 40 µg/day, e.g. about 3 µg/day to about 30 µg/day.

Embodiment 10

Use of a FXR agonist of formula (I), a stereoisomer, an enantiomer, a pharmaceutically acceptable salt thereof or an amino acid conjugate thereof, e.g. Compound A or an amino acid conjugate thereof, in the manufacture of a medicament for treating or preventing a condition mediated by Farnesoid X receptor (FXR), wherein the FXR agonist is to be administered at a dose of about 3 µg, about 4 µg, about 5 µg, about 10 µg, about 20 µg, about 25 µg, about 30 µg, about 40 µg, about 60 µg, about 90 µg, or about 120 µg. Such doses may be for daily administration (e.g. daily doses) or twice daily administration.

Embodiment 11

A FXR agonist of formula (I), a stereoisomer, an enantiomer, a pharmaceutically acceptable salt thereof or an amino acid conjugate thereof, e.g. Compound A, e.g. in free form or an amino acid conjugate thereof, for use in treating or preventing a condition mediated by FXR; wherein the FXR agonist is to be administered at a dose (e.g. daily dose)

of about 3 µg, to about 120 µg, about 5 µg, to about 120 µg, e.g. about 10 µg, to about 120 µg, e.g. about 20 µg, to 100 µg, e.g. about 30 µg, to about 90 µg, e.g. about 40 µg, to about 60 µg; or at a dose of about 10 µg, to about 60 µg, e.g. about 10 µg, to about 40 µg, e.g. about 20 µg, to about 40 µg; or at a dose of about 20 µg, to about 60 µg, e.g. about 30 µg, to about 60 µg; or at a dose of about 5 µg, to about 60 µg, e.g. about 5 µg, to about 40 µg; or at a dose of about 3 µg, to 40 µg, e.g. about 3 µg, to 30 µg, and wherein said condition mediated by FXR is non-alcoholic fatty liver disease (NAFLD), non-alcoholic steatohepatitis (NASH), drug-induced bile duct injury, gallstones, liver cirrhosis, alcohol-induced cirrhosis, cystic fibrosis, bile duct obstruction, cholelithiasis, liver fibrosis.

Embodiment 12

A FXR agonist of formula (I), a stereoisomer, an enantiomer, a pharmaceutically acceptable salt thereof, or in free form or an amino acid conjugate thereof, e.g. Compound A, e.g in free form or an amino acid conjugate thereof, for use in treating or preventing a condition mediated by FXR; wherein the FXR agonist is to be administered at a dose of about 3 µg, about 4 µg, about 5 µg, about 10 µg, about 20 µg, about 25 µg, about 30 µg, about 40 µg, about 60 µg, about 90 µg, or about 120 µg. Such doses may be for daily administration (e.g. daily doses). Such doses may be for twice daily administration.

Embodiment 13

The use of a FXR agonist of formula (I), a stereoisomer, an enantiomer, a pharmaceutically acceptable salt thereof or an amino acid conjugate thereof, e.g. Compound A or an amino acid conjugate thereof, according to any one of Embodiments 1 to 12, wherein the condition mediated by FXR is non-alcoholic fatty liver disease (NAFLD), non-alcoholic steatohepatitis (NASH), drug-induced bile duct injury, gallstones, liver cirrhosis, alcohol-induced cirrhosis, cystic fibrosis, bile duct obstruction, cholelithiasis, liver fibrosis.

Embodiment 14

The use of a FXR agonist of formula (I), a stereoisomer, an enantiomer, a pharmaceutically acceptable salt thereof or an amino acid conjugate thereof, e.g. Compound A or an amino acid conjugate thereof, according to any one of Embodiments 1 to 12, wherein the condition mediated by FXR is NAFLD or NASH.

Embodiment 15

A method for treating or preventing a condition mediated by Farnesoid X receptor (FXR) in a subject suffering therefrom, comprising administering to the subject a FXR agonist of formula (I), a stereoisomer, an enantiomer, a pharmaceutically acceptable salt thereof or an amino acid conjugate thereof, e.g. Compound A or an amino acid conjugate thereof; wherein said FXR agonist is to be administered at a daily dose of about 3 µg, to about 120 µg, about 5 µg, to about 120 µg, e.g. about 10 µg, to about 120 µg, e.g. about 20 µg, to 100 µg, e.g. about 30 µg, to about 90 µg, e.g. about 40 µg, to about 60 µg; or at a dose of about 10 µg, to about 60 µg, e.g. about 10 µg, to about 40 µg, e.g. about 20 µg, to about 40 µg; or at a dose of about 20 µg, to about 60 µg, e.g. about 30 µg, to about 60 µg; or at a dose of about 5 µg, to about 60 µg, e.g. about 5 µg, to about 40 µg, e.g. about 10 µg, to about 100 µg, e.g. about 20 µg, to about 100 µg, e.g. about 30 µg, to about 90 µg; e.g. about 3 µg, to about 40 µg, e.g. about 3 µg, to about 30 µg.

Embodiment 16

A method for treating or preventing a condition mediated by Farnesoid X receptor (FXR) in a subject suffering therefrom, comprising administering to the subject a FXR agonist of formula (I), a stereoisomer, an enantiomer, a pharmaceutically acceptable salt thereof or an amino acid conjugate thereof, e.g. Compound A or an amino acid conjugate thereof; wherein said FXR agonist is to be administered at a dose of about 3 µg/day to 120 µg/day, e.g. about 5 µg/day to 120 µg/day, e.g. about 10 µg, to about 120 µg/day, e.g. about 20 µg/day to about 100 µg/day, e.g. about 30 µg/day to about 90 µg/day, e.g. about 3 µg/day to about 30 µg/day.

Embodiment 17

A method for treating or preventing a condition mediated by Farnesoid X receptor (FXR) in a subject suffering therefrom, comprising administering to the subject a FXR agonist of formula (I), a stereoisomer, an enantiomer, a pharmaceutically acceptable salt thereof or an amino acid conjugate thereof, e.g. Compound A or an amino acid conjugate thereof; wherein said FXR agonist is to be administered at a dose of about 3 µg/day, about 4 µg/day, about 10 µg/day, about 20 µg/day, about 25 µg/day, about 30 µg/day, about 60 µg/day, about 90 µg/day or about 120 µg.

Embodiment 18

A method for treating or preventing a condition mediated by Farnesoid X receptor (FXR) according to any one of Embodiments 1 to 16, wherein the condition is a chronic liver disease, such as e.g. non-alcoholic fatty liver disease (NAFLD), non-alcoholic steatohepatitis (NASH), drug-induced bile duct injury, gallstones, liver cirrhosis, alcohol-induced cirrhosis, cystic fibrosis, bile duct obstruction, cholelithiasis, or liver fibrosis.

Embodiment 19

A method for treating or preventing a chronic liver disease, in a subject suffering therefrom, comprising administering to the subject a FXR agonist of formula (I), a stereoisomer, an enantiomer, a pharmaceutically acceptable salt thereof or an amino acid conjugate thereof, e.g. Compound A or an amino acid conjugate thereof, in a dose (e.g. daily dose) of about 3 µg, to about 100 µg, about 5 µg, to about 100 µg, e.g. about 10 µg, to about 100 µg, e.g. about 20 µg, to 100 µg, e.g. about 30 µg, to about 90 µg, e.g. about 40 µg, to about 60 µg; or at a dose of about 10 µg, to about 60 µg, e.g. about 10 µg, to about 40 µg, e.g. about 20 µg, to about 40 µg; or at a dose of about 20 µg, to about 60 µg, e.g. about 30 µg, to about 60 µg; or at a dose of about 5 µg, to about 60 µg, e.g. about 5 µg, to about 40 µg, e.g. about 10 µg, to about 100 µg, e.g. about 20 µg, to about 100 µg, e.g. about 30 µg, to about 90 µg.

Embodiment 20

A method for treating or preventing a chronic liver disease in a subject suffering therefrom, comprising administering to the subject a FXR agonist of formula (I), a stereoisomer, an enantiomer, a pharmaceutically acceptable salt thereof or an amino acid conjugate thereof, e.g. Compound A or an amino acid conjugate thereof, at a dose of about 3 µg, about 4 µg, about 5 µg, about 10 µg, about 20 µg, about 25 µg, about 30 µg, about 40 µg, about 60 µg, about 90 µg, or about 120 µg. Such doses may be for daily administration (e.g. daily doses). Such doses may be for twice daily administration.

Embodiment 21

A method according to Embodiment 19 or 20 for treating or preventing a liver disease or disorder selected from non-alcoholic fatty liver disease (NAFLD), non-alcoholic steatohepatitis (NASH), drug-induced bile duct injury, gallstones, liver cirrhosis, alcohol-induced cirrhosis, cystic fibrosis, bile duct obstruction, cholelithiasis and liver fibrosis.

Embodiment 22

A method according to Embodiment 19 or 20 for treating or preventing NASH.

Embodiment 23

A use, a FXR agonist or a method for treating or preventing a condition mediated by Farnesoid X receptor (FXR), e.g. a chronic liver disease, in a subject suffering therefrom according to any one of Embodiments 1 to 22, wherein the FXR agonist compound is to be administered for a period of 3 months to lifelong, e.g. 6 months to lifelong, e.g. 1 year to lifelong, e.g. for a period of 3 months to 1 year, e.g. 6 months to lifelong, e.g. for a period of 3 months, 6 months or 1 year or for lifelong.

Embodiment 24

A use, a FXR agonist or a method according to any one of Embodiments 1 to 23, for treating or preventing a liver disease or disorder selected from non-alcoholic fatty liver disease (NAFLD), non-alcoholic steatohepatitis (NASH), drug-induced bile duct injury, gallstones, liver cirrhosis, alcohol-induced cirrhosis, cystic fibrosis, bile duct obstruction, cholelithiasis and liver fibrosis.

Embodiment 25

A use, a FXR agonist or a method according to any one of Embodiments 1 to 23, for treating or preventing non-alcoholic steatohepatitis (NASH), wherein NASH is confirmed based on liver biopsy obtained 2 years or less before treatment initiation with Compound A (also called biopsy-proven NASH) and NASH is mild to moderate with fibrosis level F2-F3.

Embodiment 26

A use, a FXR agonist or a method according to any one of Embodiments 1 to 23, for treating or preventing non-alcoholic steatohepatitis (NASH), wherein presence of NASH has been demonstrated by:
i) by one of the following: Histologic evidence of NASH based on liver biopsy obtained 2 years or less before treatment with a FXR agonist according to any one of Embodiments 1 to 23, with a diagnosis consistent with NASH, fibrosis level F1, F2 or F3, no diagnosis of alternative chronic liver diseases and ALT≥60 IU/L (males) or ≥40 IU/L (females), or
ii) Phenotypic diagnosis of NASH based on presence of all three of the following:
ALT≥60 IU/L (males) or ≥40 IU/L (females) and
BMI≥27 kg/m2 (in patients with a self-identified race other than Asian) or ≥23 kg/m2 (in patients with a self-identified Asianrace) and
Diagnosis of Type 2 diabetes mellitus by having either: HbA1C≥6.5% or Drug therapy for Type 2 diabetes mellitus.

Embodiment 27

A pharmaceutical unit dosage form composition comprising about 10 µg, about 30 µg, about 60 µg, about 90 µg, or about 120 µg, of Compound A suitable for oral administration up to a maximum total dose of 100 µg per day. Such unit dosage form compositions may be in a form selected from a liquid, a tablet, a capsule. Also these unit dosage form compositions are for use in treating a chronic liver disease, e.g. non-alcoholic fatty liver disease (NAFLD), non-alcoholic steatohepatitis (NASH), drug-induced bile duct injury, gallstones, liver cirrhosis, alcohol-induced cirrhosis, cystic fibrosis, bile duct obstruction, cholelithiasis, liver fibrosis, e.g. for use in treating non-alcoholic steatohepatitis (NASH), e.g. for use in treating phenotypic non-alcoholic steatohepatitis (NASH).

Embodiment 28

A use, a FXR agonist or a method according to any one of Embodiments 1 to 26, a pharmaceutical unit dosage form of Embodiment 27, is administered to humans in a fasting state, e.g. administration in a fasting state, at least 30 minutes prior to first beverage, apart from water, and at least 60 minutes prior to the first meal of the day.

DETAILED DESCRIPTION OF THE INVENTION

Definitions

For purposes of interpreting this specification, the following definitions will apply and whenever appropriate, terms used in the singular will also include the plural and vice versa.

As used herein, the term "about" in relation to a numerical value x means+/−10%, unless the context dictates otherwise.

As used herein, the term "FXR agonist" refers to an agent that directly binds to and upregulates the activity of FXR.

As used herein, the term "pharmaceutically acceptable" means a nontoxic material that does not interfere with the effectiveness of the biological activity of the active ingredient(s).

As used herein, the term "amino acid conjugate" refers to conjugates of the compound of Formula (I) with any suitable amino acid. Preferably, such suitable amino acid conjugates of the compound of Formula (I) will have the added advantage of enhanced integrity in bile or intestinal fluids. Suitable amino acids include but are not limited to glycine, taurine and acylglucuronide. Thus, the present invention encompasses the glycine, taurine and acylglucuronide conjugates of the compound of Formula (I), e.g. glycine, taurine and acylglucuronide conjugates of Compound A.

As used herein, the term "subject" or "subject" refers to a human.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the subject. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the onset or development or progression of the disease or disorder.

As used herein, the term "therapeutically effective amount" refers to an amount of the compound of the invention, e.g. compound of formula (I) or a pharmaceutically acceptable salt thereof, e.g. Compound A, which is sufficient to achieve the stated effect. Accordingly, a therapeutically effective amount of a FXR agonist of formula (I), a stereoisomer, an enantiomer, a pharmaceutically acceptable salt thereof or an amino acid conjugate thereof, e.g. Compound A or an amino acid conjugate thereof, used for the treatment or prevention of a condition mediated by FXR will be an amount sufficient for the treatment or prevention of the condition mediated by FXR.

By "therapeutic regimen" is meant the pattern of treatment of an illness, e.g., the pattern of dosing used during the treatment of the disease or disorder.

As used herein, a subject is "in need of" a treatment if such subject would benefit biologically, medically or in quality of life from such treatment.

As used herein, the term "liver disease or disorder" encompasses one, a plurality, or all of non-alcoholic fatty liver disease (NAFLD), non-alcoholic steatohepatitis (NASH), drug-induced bile duct injury, gallstones, liver cirrhosis, alcohol-induced cirrhosis, cystic fibrosis, bile duct obstruction, cholelithiasis and liver fibrosis.

As used herein, a NASH phenotype or phenotypic NASH can be described using combinations of several features of metabolic syndrome (obesity, Type 2 diabetes mellitus) along with elevated ALT/AST and fatty infiltration of the liver As used herein, a "therapeutically effective amount" refers to an amount of compound of formula (I), a stereoisomer, an enantiomer, a pharmaceutically acceptable salt thereof or an amino acid conjugate thereof, e.g. Compound A or an amino acid conjugate thereof, e.g. Compound A, that is effective, upon single or multiple dose administration to a subject (such as a human subject) at treating, preventing, curing, delaying, reducing the severity of, ameliorating at least one symptom of a disorder or recurring disorder, or prolonging the survival of the subject beyond that expected in the absence of such a treatment.

MODES OF CARRYING OUT THE INVENTION

The present invention provides the use of FXR agonists for treating or preventing liver disease and disorders.

The disclosed FXR antagonists, e.g. Compound A, are useful for the treatment, prevention, or amelioration of liver diseases and disorders.

The FXR agonists, e.g. Compound A, may be used in vitro, ex vivo, or incorporated into pharmaceutical compositions and administered to individuals (e.g. human subjects) in vivo to treat, ameliorate, or prevent liver diseases and disorders. A pharmaceutical composition will be formulated to be compatible with its intended route of administration (e.g., oral compositions generally include an inert diluent or an edible carrier). Other nonlimiting examples of routes of administration include parenteral (e.g., intravenous), intradermal, subcutaneous, oral (e.g., inhalation), transdermal (topical), transmucosal, and rectal administration. The pharmaceutical compositions compatible with each intended route are well known in the art. Exemplary pharmaceutical compositions comprising an FXR agonist of formula (I), e.g. Compound A are described in WO2012/087519.

The frequency of dosing may be twice per day, once per day, or every two days, e.g. once a day. In some embodiments the frequency of dosing is twice per day. The dosing frequency will depend on, inter alia, the phase of the treatment regimen.

In some embodiments, the dosing regimen comprises administration of an FXR agonist of formula (I), e.g. Compound A, about 3 μg, about 120 μg, delivered orally, e.g. about 5 μg-about 120 μg, delivered orally, e.g. about 10 μg, about 120 μg, delivered orally, e.g. about 20 μg-100 μg delivered orally, e.g. about 30 μg-about 90 μg, delivered orally, e.g. about 40 μg-about 60 μg, delivered orally. Such doses may be for daily administration (daily doses), or twice daily administration or every two days administration, e.g. for daily administration.

In some embodiments, the dosing regimen comprises administration of an FXR agonist of formula (I), e.g. Compound A, at a dose in a range of about 20 μg-about 60 μg, delivered orally, e.g. about 30 μg-about 60 μg, delivered orally. Such doses may be for daily administration (daily doses), or twice daily administration or every two days administration, e.g. for daily administration.

In some embodiments, the dosing regimen comprises administration of an FXR agonist of formula (I), e.g. Compound A, about 10 μg-60 μg, delivered orally, e.g. about 10 μg-about 40 μg, delivered orally, e.g. about 20 μg-about 40 μg, delivered orally. Such doses may be for daily administration (daily doses), or twice daily administration or every two days administration, e.g. for daily administration.

In some embodiments, the dosing regimen comprises administration of an FXR agonist of formula (I), e.g. Compound A, at a dose in a range of about 5 μg-about 60 μg, delivered orally, e.g. about 5 μg-about 40 μg, delivered orally. Such doses may be for daily administration (daily doses), or twice daily administration or every two days administration, e.g. for daily administration.

In some embodiments, the dosing regimen comprises administration of an FXR agonist of formula (I), e.g. Compound A, at a dose in a range of about 3 μg-about 40 μg, delivered orally, e.g. about 3 μg-about 30 μg, delivered orally. Such doses may be for daily administration (daily doses), or twice daily administration or every two days administration, e.g. for daily administration.

In some embodiments, the dosing regimen comprises administration of an FXR agonist of formula (I), e.g. Compound A, at a dose of about 3 µg, delivered orally, about 4 µg, delivered orally, about 5 µg, delivered orally, about 10 µg, delivered orally, about 20 µg, delivered orally, about 25 µg, delivered orally, about 30 µg, delivered orally, about 40 µg, delivered orally, about 60 µg, delivered orally, or about 90 µg, delivered orally. Such doses may be oral administration.

In some embodiments, the dosing regimen comprises administration of an FXR agonist of formula (I), e.g. Compound A, at a dose in a range of about 3 µg/day to about 120 µg/day, e.g. about 5 µg/day to about 120 µg/day, e.g. about 10 µg/day to about 120 µg/day, e.g. about 20 µg/day to 100 µg/day, e.g. about 30 µg/day to about 90 µg/day, e.g. about 40 µg/day to about 60 µg/day, e.g. about 10 µg/day to 60 µg/day, e.g. about 10 µg/day to about 40 µg/day, e.g. about 20 µg/day to 40 µg/day, e.g. about 20 µg/day to about 60 µg/day, e.g. about 30 µg/day to about 60 µg/day, e.g. about 5 µg/day to 60 µg/day, e.g. about 5 µg/day to 40 µg/day, e.g. about 3 µg/day to about 40 µg/day, about 3 µg/day to about 30 µg/day.

In some embodiments, the dosing regimen comprises administration of a FXR agonist of formula (I), e.g. Compound A, at a dose of about 3 µg/day, about 4 µg/day, about 5 µg/day, about 10 µg/day, about 25 µg/day, about 30 µg/day, about 60 µg/day, about 90 µg/day or about 120 µg. Such regimens may be delivered orally.

In some embodiments, the dosing regimen comprises administration of a FXR agonist of formula (I), e.g. Compound A, at a dose of about 3 µg, twice daily, about 4 µg, twice daily, about 5 µg, twice daily, about 10 µg, twice daily, about 25 µg, twice daily, about 30 µg, twice daily. Such regimens may be delivered orally.

In some embodiments, the dosing regimen comprises administration of a FXR agonist of formula (I), e.g. Compound A, at a dose of about 5 µg, every two days, about 10 µg, every two days, about 40 µg, every two days, about 60 µg, every two days. Such regimens may be delivered orally.

Disclosed herein are methods of treating or preventing a liver disease or disorder as herein above defined, comprising administering a subject in need thereof a FXR agonist of formula (I), e.g. Compound A, at a dose of about 3 µg, to about 100 µg, about 5 µg, to about 100 µg, e.g. about 10 µg, to about 100 µg, e.g. about 20 µg, to 100 µg, e.g. about 30 µg, to about 90 µg, e.g. about 40 µg, to about 60 µg, e.g. about 10 µg, to 60 µg, e.g. about 10 µg, to about 40 µg, e.g. about 20 µg, to about 40 µg; or a dose of about 20 µg, to about 60 µg, e.g. about 30 µg, to about 60 µg; or a dose of about 5 µg, to about 60 µg, e.g. about 5 µg, to about 40 µg, e.g. about 3 µg, to about 40 µg, e.g. about 3 µg, to about 30 µg.

Disclosed herein are methods of treating or preventing a liver disease or disorder as herein above defined, comprising administering a subject in need thereof a FXR agonist of formula (I), e.g. Compound A, at about 3 µg, e.g at about 4 µg, e.g at about 5 µg, e.g about 10 µg, e.g. about 20 µg, e.g. about 25 µg, e.g. about 30 µg, e.g. about 40 µg, e.g about 60 µg, or e.g. about 90 µg. In some embodiments such a dose is administered daily, e.g. orally. In some embodiments such a dose is administered orally, e.g. daily.

Disclosed herein are FXR agonists of formula (I), a stereoisomer, an enantiomer, a pharmaceutically acceptable salt thereof or an amino acid conjugate thereof, e.g. Compound A or an amino acid conjugate thereof, e.g. Compound A, for use in treating or preventing a liver disease or disorder as herein above defined, characterized in that said FXR agonist is to be administered at a dose selected from the group consisting of about 3 µg, about 4 µg, about 5 µg, about 10 µg, about 20 µg, about 25 µg, about 30 µg, about 40 µg, about 60 µg, and about 90 µg. Such doses may be administered daily, twice daily or every two days, e.g. daily. Such doses may be administered orally.

In some embodiments, are disclosed FXR agonists of formula (I), a stereoisomer, an enantiomer, a pharmaceutically acceptable salt thereof or an amino acid conjugate thereof, e.g. Compound A or an amino acid conjugate thereof, e.g. Compound A, for use in treating or preventing a liver disease or disorder as herein above defined, wherein said FXR agonist is to be administered at a daily dose selected from the group consisting of about 10 µg, about 20 µg, about 25 µg, about 30 µg, about 60 µg, about 90 µg, and about 120 µg.

In some embodiments, are disclosed FXR agonists of formula (I), a stereoisomer, an enantiomer, a pharmaceutically acceptable salt thereof or an amino acid conjugate thereof, e.g. Compound A or an amino acid conjugate thereof, e.g. Compound A, for use in treating or preventing a liver disease or disorder as herein above defined, wherein said FXR agonist is to be administered at a daily dose selected from the group consisting of about 3 µg, about 4 µg, about 5 µg, about 10 µg, about 30 µg.

In some embodiments, are disclosed FXR agonists of formula (I), a stereoisomer, an enantiomer, a pharmaceutically acceptable salt thereof or an amino acid conjugate thereof, e.g. Compound A or an amino acid conjugate thereof, e.g. Compound A, for use in treating or preventing a liver disease or disorder as herein above defined, wherein said FXR agonist is to be administered twice daily at a dose selected from the group consisting of about 3 µg, about 4 µg, about 5 µg, about 10 µg, about 25 µg, about 30 µg.

In some embodiments, are disclosed FXR agonists of formula (I), a stereoisomer, an enantiomer, a pharmaceutically acceptable salt thereof or an amino acid conjugate thereof, e.g. Compound A or an amino acid conjugate thereof, e.g. Compound A, for use in treating or preventing a liver disease or disorder as herein above defined, wherein said FXR agonist is to be administered every two days at a dose selected from the group consisting of about 5 µg, about 10 µg, about 40 µg, about 60 µg.

In some embodiments, are disclosed FXR agonists of formula (I), a stereoisomer, an enantiomer, a pharmaceutically acceptable salt thereof or an amino acid conjugate thereof, e.g. Compound A or an amino acid conjugate thereof, e.g. Compound A, for use in treating or preventing a liver disease or disorder as herein above defined, wherein said FXR agonist is to be administered at a daily dose of about 3 µg, or about 5 µg.

In some embodiments, are disclosed FXR agonists of formula (I), a stereoisomer, an enantiomer, a pharmaceutically acceptable salt thereof or an amino acid conjugate thereof, e.g. Compound A or an amino acid conjugate thereof, e.g. Compound A, for use in treating or preventing a liver disease or disorder as herein above defined, wherein said FXR agonist is to be administered at a daily dose of about 10 µg.

In some embodiments, are disclosed formula (I), a stereoisomer, an enantiomer, a pharmaceutically acceptable salt thereof or an amino acid conjugate thereof, e.g. Compound A or an amino acid conjugate thereof, e.g. Compound A, for use in treating or preventing a liver disease or disorder as herein above defined, wherein said FXR agonist is to be administered at a daily dose of about 20 µg, or 25 µg.

In some embodiments, are disclosed FXR agonists of formula (I), a stereoisomer, an enantiomer, a pharmaceutically acceptable salt thereof or an amino acid conjugate thereof, e.g. Compound A or an amino acid conjugate thereof, e.g. Compound A, for use in treating or preventing a liver disease or disorder as herein above defined, wherein said FXR agonist is to be administered at a daily dose of about 30 µg.

In some embodiments, are disclosed FXR agonists of formula (I) or pharmaceutically acceptable salts thereof, e.g. Compound A, for use in treating or preventing a liver disease or disorder as herein above defined, wherein said FXR agonist is to be administered at a daily dose of about 40 µg.

In some embodiments, are disclosed FXR agonists of formula (I), a stereoisomer, an enantiomer, a pharmaceutically acceptable salt thereof or an amino acid conjugate thereof, e.g. Compound A or an amino acid conjugate thereof, e.g. Compound A, for use in treating or preventing a liver disease or disorder as herein above defined, wherein said FXR agonist is to be administered at a daily dose of about 60 µg.

In some embodiments, there is provided dosing regimens that provide a Cmax of the FXR agonist of formula (I) or pharmaceutically acceptable salt thereof, e.g. Compound A, of at least about 0.2 ng/mL, e.g. in a range of about 0.2 to about 2.0 ng/mL, e.g. about 0.2 to about 1.0 ng/mL, e.g. about 0.2 to about 0.5 ng/mL.

In some embodiments, there is provided Compound A at a daily dose of about 10 µg, of about 30 µg, of about 60 µg, of about 90 µg, or of about 120 µg.

In some embodiments, there is provided Compound A at a daily dose of about 10 µg, of about 30 µg, of about 60 µg, or of about 90 µg, for use in treating a chronic liver disease, e.g. non-alcoholic fatty liver disease (NAFLD), non-alcoholic steatohepatitis (NASH), drug-induced bile duct injury, gallstones, liver cirrhosis, alcohol-induced cirrhosis, cystic fibrosis, bile duct obstruction, cholelithiasis, liver fibrosis, e.g. for use in treating non-alcoholic steatohepatitis (NASH) or for use in treating phenotypic NASH.

In some embodiments, there is provided a pharmaceutical unit dosage form composition comprising about 10 µg, about 30 µg, about 60 µg, or about 90 µg of Compound A suitable for oral administration up to a maximum total dose of 100 µg per day. Such dosage forms are selected from a liquid, a tablet, a capsule. The dosage forms are for use in treating a chronic liver disease, e.g. non-alcoholic fatty liver disease (NAFLD), non-alcoholic steatohepatitis (NASH), drug-induced bile duct injury, gallstones, liver cirrhosis, alcohol-induced cirrhosis, cystic fibrosis, bile duct obstruction, cholelithiasis, liver fibrosis, e.g. for use in treating non-alcoholic steatohepatitis (NASH).

In some embodiments, there is provided Compound A at a daily dose of about 10 µg, of about 30 µg, of about 60 µg, or of about 120 µg, for use in treating a chronic liver disease, e.g. non-alcoholic fatty liver disease (NAFLD).

In some embodiments, there is provided Compound A at a daily dose of about 10 µg, of about 30 µg, of about 60 µg, or of about 120 µg, for use in treating non-alcoholic steatohepatitis (NASH).

In some embodiments, there is provided Compound A administration once daily, morning in a fasting state, at least 30 minutes prior to first beverage, apart from water, and at least 60 minutes prior to the first meal of the day.

In some embodiments, there is provided Compound A administration once daily, morning in a fasting state, at least 30 minutes prior to first beverage, apart from water, and at least 60 minutes prior to the first meal of the day; e.g. in an amount of about 10 µg, about 30 µg, about 60 µg, about 90 µg, or about 120 µg.

In some embodiments, there is provided Compound A at a daily dose of about 10 µg, of about 30 µg, of about 60 µg, or of about 120 µg, for use in treating non-alcoholic steatohepatitis (NASH) once daily, and Compound A is to be administered morning in a fasting state, at least 30 minutes prior to first beverage, apart from water, and at least 60 minutes prior to the first meal of the day.

Kits for the Treatment of Liver Disease or Disorders

Provided herein are kits useful for providing FXR agonists of formula (I), a stereoisomer, an enantiomer, a pharmaceutically acceptable salt thereof or an amino acid conjugate thereof, e.g. Compound A or an amino acid conjugate thereof, e.g. Compound A, for the treatment of a liver disease or disorder as herein above defined. Such kits may comprise FXR agonists of formula (I), a stereoisomer, an enantiomer, a pharmaceutically acceptable salt thereof or an amino acid conjugate thereof, e.g. Compound A or an amino acid conjugate thereof, e.g. Compound A, or a pharmaceutical composition comprising said FXR agonist, e.g. Compound A. Additionally, such kits may comprise means for administering the FXR agonist molecule (e.g. solid composition) and instructions for use.

Accordingly, disclosed herein are kits comprising: a) a pharmaceutical composition comprising a therapeutically effective amount of a FXR agonist formula (I), a stereoisomer, an enantiomer, a pharmaceutically acceptable salt thereof or an amino acid conjugate thereof, e.g. Compound A or an amino acid conjugate thereof, e.g. Compound A; b) means for administering the FXR agonist molecule (e.g. Compound A) to a subject a liver disease or disorder as herein above defined; and c) instructions for use, wherein the pharmaceutical composition comprises said FXR agonist molecule at dose (e.g. daily dose) in a range of about 3 µg, to about 100 µg, about 5 µg, to about 100 µg, e.g. about 10 µg, to about 100 µg, e.g. about 20 µg, to 100 µg, e.g. about 30 µg, to about 90 µg, e.g. about 40 µg, to about 60 µg, e.g. about 10 µg, to 60 µg, e.g. about 10 µg, to 40 µg, e.g. about 20 µg, to 40 µg, e.g. about 20 µg, to about 60 µg, e.g. about 30 µg, to about 60 µg; or at a dose (e.g. daily dose) in a range of about 5 µg, to about 40 µg, e.g. about 10 µg, to about 40 µg, e.g. about 20 µg, to about 40 µg, e.g. about 3 µg, to about 40 µg, about 3 µg, to about 30 µg.

Are also disclosed kits comprising: a) a pharmaceutical composition comprising a therapeutically effective amount of a FXR agonist of formula (I), a stereoisomer, an enantiomer, a pharmaceutically acceptable salt thereof or an amino acid conjugate thereof, e.g. Compound A or an amino acid conjugate thereof, e.g. Compound A; b) means for administering the FXR agonist molecule (e.g. Compound A) to a subject having a liver disease or disorder as herein above defined; and c) instructions for use, wherein the pharmaceutical composition comprises a dose of the FXR agonist molecule selected from the group consisting of about 3 µg, about 4 µg, about 5 µg, about 10 µg, about 20 µg, about 25 µg, about 30 µg, about 40 µg, about 60 µg, and about 90 µg; e.g. wherein the pharmaceutical composition comprises about 3 µg, about 4 µg, about 5 µg, about 10 µg, about 20 µg, about 25 µg, about 30 µg, about 40 µg, about 60 µg, or about 90 µg, of the FXR agonist molecule.

In another embodiment, a FXR agonist of formula (I), a stereoisomer, an enantiomer, a pharmaceutically acceptable salt thereof or an amino acid conjugate thereof, e.g. Compound A or an amino acid conjugate thereof, e.g. Compound A, is administered enterally; and more particularly, orally.

Unless specified otherwise, a compound for use in the methods of the invention refers to a FXR agonist of formula (I), a stereoisomer, an enantiomer, a pharmaceutically acceptable salt thereof or an amino acid conjugate thereof, e.g. Compound A or an amino acid conjugate thereof, prodrugs, and inherently formed moieties (e.g., polymorphs, solvates and/or hydrates). Any formula given herein is also intended to represent unlabeled forms as well as isotopically labeled forms of the compounds.

EXAMPLES

Example 1

Effect of Test Compound in Chronic Treatment Rat ANIT Model

Compound A was evaluated in a chronic treatment model of cholestasis over a range of doses from 0.01 to 3 mg/kg.

Rats were treated with alpha-naphthyl-isothiocyanate (ANIT) (0.1% w/w) in food for 3 days prior to treatment with the compound at the indicated doses or with vehicle control ("Veh"). A non-cholestatic control group was fed standard chow diet without ANIT, and serve as the non-cholestatic control animals ("Control"). After 14 days of oral dosing, the indicated analyte was measured in serum. LLQ, lower limit of quantitation. Mean±SEM; n=5.

ANIT treatment caused elevation of hepatobiliary injury indicators, such as elevated levels of circulating aspartate aminotransferase (AST) (FIG. 1A), alanine aminotransferase (ALT) (FIG. 1B), bilirubin (FIG. 1C) and bile acids (FIG. 1D) ("Veh" vs "Control"). These data demonstrate that ANIT exposure induced profound cholestasis and hepatocellular damage. In contrast, Compound A improved many of these indicators starting at doses as low as 0.01 mg/kg. Marked reductions of serum bile acid and bilirubin concentrations were observed upon treatment with Compound A. The reduced levels of total bile acids (TBA) levels associated with treatment of Compound A were consistent with the pharmacological action of FXR agonist by reducing accumulation of bile acids in the liver, enhancing bile acid excretion in the biliary tract and inhibiting bile acid synthesis. The improvement in the serum conjugated bilirubin (a direct indicator for hepatic function) by Compound A implies recovery from cholestasis with improved bile excretion.

Furthermore, Compound A stimulated serum FGF15 expression in the chronic treatment rat ANIT model in a dose dependent manner (FIG. 1E). Serum FGF15 levels were quantified using an FGF15 Meso Scale Discovery (MSD) assay. Mouse FGF15 antibody from R&D Systems (AF6755) was used both as capture and detection antibody in the assay. MSD SULFO-TAG NHS-Ester was used to label the FGF15 antibody. MSD standard 96-well plates were coated with the FGF15 capture antibody and the plates were blocked with MSD Blocker A (R93AA-2). After washing the plate with PBS+0.05% Tween 20, MSD diluent 4 was dispensed into each well and incubated for 30 min. 25 µl of calibrator dilutions or samples (serum or EDTA plasma) were dispensed into each well and incubated with shaking at RT. After washing, detection antibody was added and incubated with shaking for 1 h at RT. After washing and the addition of MSD Read buffer (R92TC-2), the plate was read on an MSD SECTOR Imager 6000. Plots of the standard curve and unknown samples were calculated using MSD data analysis software.

Activation of FXR in the ileum induces the expression of fibroblast growth factor 15 (FGF15 in rodent; FGF19 in human), a hormone that is secreted in the portal blood and signals to the liver to repress Cyp7a1 expression synergistically with SHP. The direct FXR-dependent induction of FGF15/19 along with FGF15/19's anti-cholestatic properties makes it a convenient serum biomarker for detecting target engagement of FXR agonists. Significant dose-dependent induction of FGF15 observed with treatment of Compound A demonstrates FXR target engagement by Compound A.

Example 2

The efficacious concentration of Compound A was determined by PK/PD modeling from the rat ANIT-induced cholestasis chronic treatment model.

Male Wistar rats were treated with ANIT (0.1% ANIT in chow diet) for 2 weeks. The treatment of Compound A (0.01, 0.05, 0.25, 1 and 3 mg/kg, n=5/group) was initiated 3 days after disease induction by ANIT. The serum samples were collected on day 14 for analysis of biomarkers of hepatobiliary injury (including ALT, AST, bilirubin and bile acids). The PK samples (pre-dose, 0.5, 1, 3, 7, 10 and 24 h, n=3/dose group) were taken on day 13 (at steady-state). AUC0-24 h was determined using Phoenix WinNonlin 6.3 software and the average concentrations were calculated from mean of AUC0-24 h at each dose (divided the AUC 0-24 h by 24 h). The mean biomarker data were compared to the PK data (average concentration at each dose) for the modeling. The IC80 was determined using the Inhibitory effect Imax model (effect C=0 at Imax, C=infinity at E0) built in Phoenix WinNonlin 6.3 software. Since the biomarkers were markedly lowered at the lowest dose in the study (0.01 mg/kg), there was variability in the IC80 determination for each biomarker. Therefore, we chose to use a mean of the IC80 for the four biomarkers (total bilirubin, total bile acids, ALT and AST) as the IC80 for efficacy in this model. From these studies, the IC80 of LJN452 was 0.127 ng/ml and the corresponding AUC0-24 h was 3.05 ng*h/ml (Table 1), and the corresponding efficacious dose is approximately 0.01 mg/kg (based on Table 1 and Table 2).

TABLE 1

Estimation of effective exposure of Compound A in rat ANIT model by PK/PD modeling

| Serum biomarkers | $E_0$ | $I_{max}$ | $IC_{80}$ of LJN452 (ng/ml) |
|---|---|---|---|
| Total bilirubin (mg/dL) | 2.3 | 2.0 | 8.223 |
| Total bile acids (µmol/L) | 147.8 | 125.5 | 0.155 |
| ALT (U/L) | 138.2 | 84.2 | 0.054 |
| AST (U/L) | 272.8 | 140.3 | 0.076 |
| Mean ($IC_{80}$) | | | 0.127 |
| Mean (efficacious $AUC_{0-24\,h}$; ng*h/ml) | | | 3.05 |

PK/PD modeling of the exposure of Compound A compared to the serum markers of hepatobiliary injury in the 2-week rat ANIT chronic treatment model. E0, effect at zero drug concentration; $I_{max}$, maximal drug effect; $IC_{80}$, drug concentration producing 80% of the maximum effect.

TABLE 2

Pharmacokinetic properties of Compound A in the
chronic 2 week rat ANIT-induced cholestasis model

| Dose mg/kg | Cmax ng/ml | AUC 0-24 hr hrs* ng/ml |
|---|---|---|
| 0.01 | 0.39 | 3.49 |
| 0.05 | 2.28 | 18.25 |
| 0.25 | 15.59 | 158.28 |
| 1.0 | 52.03 | 581.62 |
| 3.0 | ND | ND |

Compound A serum exposure in the 2 week chronic ANIT-induced cholestasis model.
Samples were collected on day 13 of the study shown in Example 1. ND = not determined.
Data are presented as mean (n = 3/group).

Example 3

The efficacious concentration of Compound A was determined by PK/PD modeling from the rat ANIT-induced cholestasis chronic treatment model described in Example 1. The PK samples (pre-dose, 0.5, 1, 3, 7, 10 and 24 h, n=3/dose group) were taken on day 13 (at steady-state). AUC0-24 h was determined using Phoenix WinNonlin 6.3 software and the average concentrations were calculated from mean of AUC0-24 h at each dose (divided the AUC0-24 h by 24 h). The individual biomarker data were compared to the PK data (average concentration at each dose) for the modeling. Since the lowest dose (0.01 mg/kg) already approached maximal efficacy, the IC80 was chosen as the measurement of the efficacious exposure (Table 1). The IC80 was determined using the Inhibitory effect Imax model (effect C=0 at Imax, C=infinity at E0) built in Phoenix WinNonlin 6.3 software. From these calculations, the average efficacious concentration of Compound A at Cmax can be estimated as 0.127 ng/ml and the AUC0-24 h as 3.05 ng*h/ml (Table 3).

TABLE 3

Estimation of effective exposure of Compound
A in rat ANIT model by PK/PD modeling

| Serum biomarkers | $E_0$ | $I_{max}$ | $IC_{80}$ of Compound A (ng/ml) |
|---|---|---|---|
| Total bilirubin (mg/dL) | 2.3 | 2.0 | 0.223 |
| Total bile acids (µmol/L) | 147.8 | 125.5 | 0.155 |
| ALT (U/L) | 138.2 | 84.2 | 0.054 |
| AST (U/L) | 272.8 | 140.3 | 0.076 |
| Mean (IC80) | | | 0.127 |
| Mean (efficacious AUC0-24 h; ng*h/ml) | | | 3.05 |

PK/PD modeling of the exposure of Compound A compared to the serum markers of hepatobiliary injury in the 2-week rat ANIT chronic treatment model.
$E_0$: effect at zero drug concentration;
$I_{max}$: maximal drug effect IC80, drug concentration producing 80% of the maximum effect.

Example 4

To characterize the dose/exposure/efficacy relationship for Compound A, regulation of FXR target genes involved in bile acid synthesis and transport was analyzed in rats.

Rats were treated for two weeks with a broad range of doses of Compound A (0.003, 0.01, 0.03, 0.1, 0.3, 1, 3 mg/kg) and subsequent gene induction (SHP, BSEP, FGF15) or repression (Cyp7a1, Cyp8b1) was determined by qRT-PCR in liver and ileum on day 14 (at t=1 and 3 hours). The effective dose (ED) calculations are described below. Both the mean ED and the median ED indicate an estimated effective dose of approximately 0.01 mg/kg.

In the liver treatment with Compound A resulted in significant, dose-dependent increases in gene expression levels of both SHP and BSEP and the levels of Cyp8b1 mRNA were potently repressed. Complete data set representing all time points and doses evaluated can be found in FIG. 2.

Figure 1:
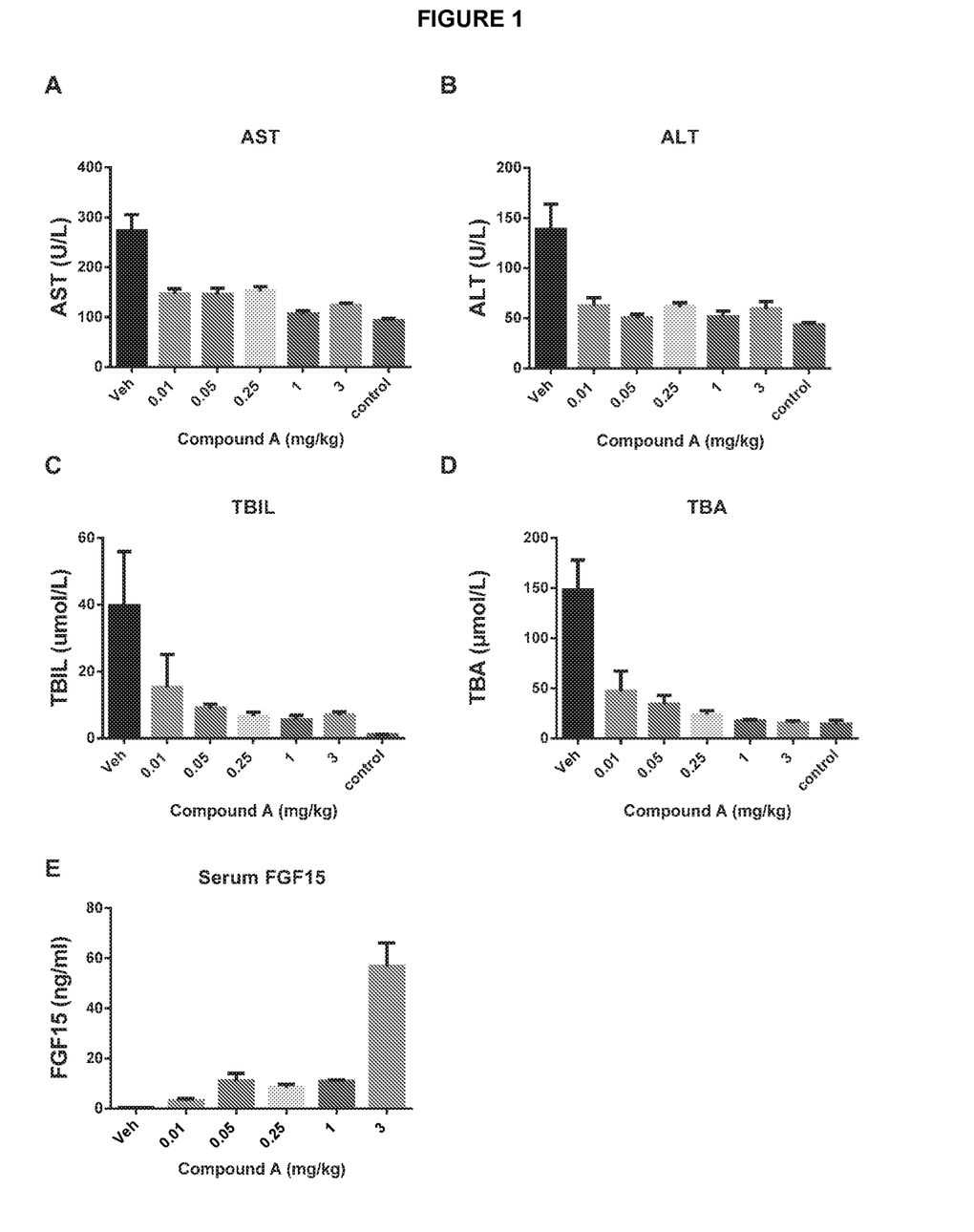
FIGS. 1A-1D show the effect of a Compound A on serum markers of cholestasis and liver damage in the chronic treatment rat ANIT model.
FIG. 1E shows serum FGF15 protein levels following treatment with Compound A in the chronic rat ANIT-induced cholestasis model.
Figure 2:
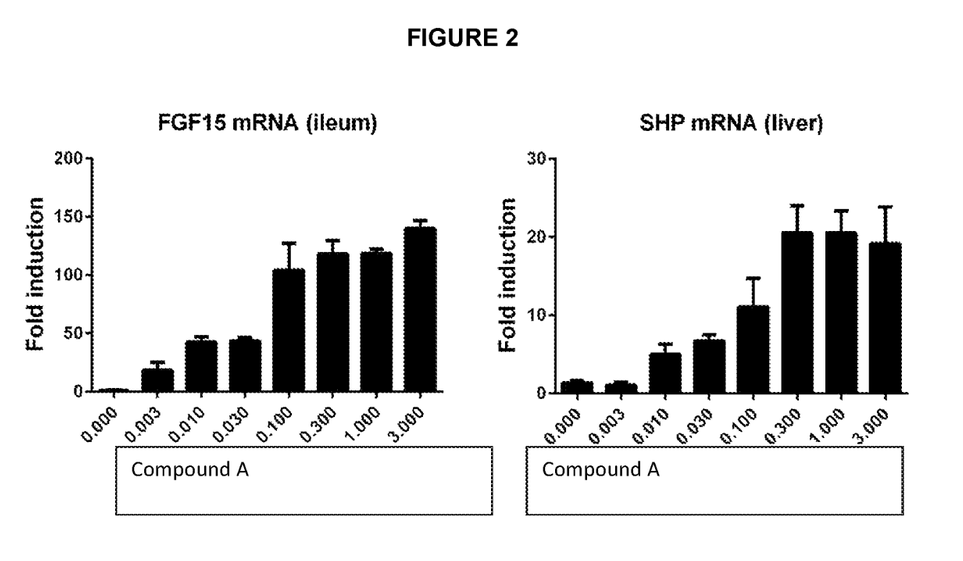
FIG. 2 show the effect of different dosages of Compound A on mRNA expression of FXR target genes in rat intestine.

The results shown in FIG. 1 and FIG. 2 are consistent with the use of a compound A for the treatment of liver disease or intestinal disease according to the dosage, e.g daily dosage, as herein above defined for humans.

Example 5

The human efficacy dose was calculated based on the efficacious exposure in the rat ANIT-induced disease model. Since the in vitro potency and protein binding between human and rat were similar, the EC80 exposure in human was assumed to be the same as that in rat (3.05 ng*h/mL).

Study Protocol:

A total of 69 healthy subjects received Compound A at doses ranging from 10 µg to 3000 µg in single or 10 µg to 100 µg in multiple daily doses.

For each subject, Compound A was determined in plasma and urine using validated LC-MS/MS methods. The lower limit of quantification (LLOQ) for Compound A was 20 pg/mL in plasma and 100 pg/mL in urine.

Following a single oral dose, the median Tmax was 4 hours with a mean apparent terminal elimination half-life ranging from 13 to 22 h. An approximately dose proportional increase was noted for mean Cmax and AUCinf in the dose range of 10 µg to 3000 µg for a single dose. Following once daily doses of Compound A for 13 days, median Tmax was at 4 h on Day 13. An approximately dose-proportional increase in Cmax and AUCtau was observed in the dose range (Table 4).

TABLE 4

Summary of Plasma Pharmacokinetic Parameters under fasting condition
Compound: Compound A; Matrix: plasma, Analyte: Compound A

| Treatment | | Tmax** (h) | Cmax (ng/mL) | AUClast (h*ng/mL) | AUCinf (h*ng/mL) | T½ (h) | CL/F (L/h) |
|---|---|---|---|---|---|---|---|
| Compound A 10 µg (fasted) | n | 5 | 5 | 5 | 4 | 4 | 4 |
| | Mean (SD) | 4.00 (3.00-6.00) | 0.186 (0.0310) | 2.79 (0.311) | 3.39 (0.333) | 14.9 (3.22) | 2.98 (0.324) |
| | CV % | 26.1 | 16.7 | 11.1 | 9.8 | 21.7 | 10.9 |
| Compound A 30 µg (fasted) | n | 6 | 6 | 6 | 5 | 5 | 5 |
| | Mean (SD) | 4.00 (3.00-6.00) | 0.627 (0.108) | 12.7 (1.04) | 13.4 (1.16) | 13.7 (4.74) | 2.26 (0.202) |
| | CV % | 27.2 | 17.2 | 8.2 | 8.7 | 34.7 | 8.9 |

TABLE 4-continued

Summary of Plasma Pharmacokinetic Parameters under fasting condition
Compound: Compound A; Matrix: plasma, Analyte: Compound A

| Treatment | | Tmax** | Cmax | AUClast | AUCinf | T½ | |
|---|---|---|---|---|---|---|---|
| CL/F | | (h) | (ng/mL) | (h*ng/mL) | (h*ng/mL) | (h) | (L/h) |
| Compound A | n | 6 | 6 | 6 | 5 | 5 | 5 |
| 100 µg (fasted) | Mean (SD) | 4.00 (4.00-4.03) | 1.73 (1.04) | 34.8 (15.6) | 37.9 (17.2) | 13.5 (3.36) | 3.08 (1.25) |
| | CV % | 0.4 | 59.8 | 44.9 | 45.4 | 24.9 | 40.4 |
| Compound A | n | 6 | 6 | 6 | 6 | 6 | 6 |
| 300 µg (fasted) | Mean (SD) | 4.00 (3.00-8.00) | 6.41 (3.24) | 119 (55.0) | 123 (56.4) | 15.3 (5.55) | 3.21 (2.30) |
| | CV % | 39.1 | 50.6 | 46.4 | 45.8 | 36.4 | 71.6 |
| Compound A | n | 6 | 6 | 6 | 5 | 5 | 5 |
| 1000 µg (fasted) | Mean (SD) | 4.00 (3.00-8.00) | 22.1 (9.37) | 416 (229) | 482 (250) | 21.9 (10.5) | 2.43 (0.917) |
| | CV % | 39.0 | 42.4 | 55.0 | 51.9 | 47.8 | 37.7 |
| Compound A | n | 6 | 6 | 6 | 6 | 6 | 6 |
| 3000 µg (fasted) | Mean (SD) | 4.00 (4.00-6.00) | 54.2 (38.2) | 888 (341) | 933 (361) | 16.5 (3.53) | 3.63 (1.35) |
| | CV % | 18.8 | 70.5 | 38.4 | 38.7 | 21.4 | 37.3 |

Multiple Oral Dose Pharmacokinetics:

With once daily oral dosing of Compound A (10 µg, 30 µg, 60 µg, 100 µg) in the fasted state for 13 days, the time to reach maximal Compound A plasma concentrations at Day 13 was similar to that of Day 1 across all doses with a median Tmax of 4 hours (range: 3-10 hours) post-dose. Steady-state was reached by Day 4 as trough levels were comparable from Day 4 and onwards up to Day 13. Consistent to the relative short t½, an accumulation ratio of less than 2-fold (1.21-1.87) was observed. An approximately dose proportional increase was noted for mean Cmax and AUCinf in the dose range of 10 µg to 100 µg. At Day 13, the inter-subject variability (CV %) ranged from approximately 20% to 40% for Cmax, and from approximately 25% to 44% for AUCtau (Table 5).

The human PK results from this study showed that the plasma exposure of Compound A was dose-proportional for doses 1-100 µg on both day 1 and day 13. The average Cmax and AUCtau at day 13 for a dose level of 10 µg (the exposures for the doses 10-100 µg were normalized to 10 µg) was calculated to be 0.32 ng/mL and 4.84 ng*h/mL, respectively. With this information, the human efficacious dose is estimated to be at least 6 µg with a Cmax of ~0.2 ng/mL (~0.3).

An approximately dose-proportional increase in Cmax and AUCtau was observed in the dose range of 10-100 µg.

Dose-dependent increases in FGF19, a biomarker of FXR target engagement in the enterocyte, were noted in single dose studies from 10 µg (median Cmax 438 µg/mL) to 1 mg Compound A (median Cmax 1820 µg/mL). At 3000 µg Compound A the median FGF19 Cmax was 1750 pg/mL.

TABLE 5

Summary of Plasma Pharmacokinetic parameters following multipleoral dose administration

| Treatment | Profile Day | | AUCtau (h*ng/mL) | Cmax (ng/mL) | Tmax** (h) | Tlast (h) | Racc |
|---|---|---|---|---|---|---|---|
| | | | Compound: Compound A; Matrix: plasma, Analyte: Compound A | | | | |
| CompoundA | 1 | n | 9 | 9 | 9 | 9 | 9 |
| 10 µg qd | | Mean (SD) | 2.88 (1.27) | 0.212 (0.109) | 4.00 (4.00-10.0) | 23.9 (0.00556) | 1.00 (0) |
| | | CV % | 43.9 | 51.7 | 37.5 | 0.0 | 0.0 |
| | 13 | n | 9 | 9 | 9 | 9 | 9 |
| | | Mean (SD) | 4.88 (1.47) | 0.319 (0.104) | 4.00 (4.00-6.00) | 23.6 (0) | 1.87 (0.609) |
| | | CV % | 30.1 | 32.7 | 21.4 | 0.0 | 32.5 |
| CompoundA | 1 | n | 6 | 6 | 6 | 6 | 6 |
| 30 µg qd | | Mean (SD) | 11.7 (3.31) | 0.894 (0.305) | 6.00 (6.00-8.00) | 23.9 (0) | 1.00 (0) |
| | | CV % | 28.2 | 34.1 | 15.5 | 0.0 | 0.0 |
| | 13 | n | 6 | 6 | 6 | 6 | 6 |
| | | Mean (SD) | 14.0 (4.37) | 0.943 (0.260) | 4.00 (4.00-10.0) | 23.6 (0.0136) | 1.21 (0.278) |
| | | CV % | 31.2 | 27.6 | 45.4 | 0.1 | 22.9 |
| Compound A | 1 | n | 6 | 6 | 6 | 6 | 6 |
| 60 µg qd | | Mean (SD) | 16.2 (5.44) | 1.22 (0.475) | 4.00 (3.00-6.00) | 23.9 (0) | 1.00 (0) |
| | | CV % | 33.5 | 39.1 | 23.6 | 0.0 | 0.0 |
| | 13 | n | 6 | 6 | 6 | 6 | 6 |
| | | Mean (SD) | 25.3 (6.40) | 1.61 (0.331) | 4.00 (3.00-6.00) | 22.3 (3.07) | 1.66 (0.560) |
| | | CV % | 25.4 | 20.5 | 31.5 | 13.7 | 33.7 |
| | | | Compound: Compound A; Matrix: plasma; Analyte: Compound A | | | | |
| CompoundA | 1 | n | 6 | 6 | 6 | 6 | 6 |
| 100 µg qd | | Mean (SD) | 30.3 (12.4) | 2.40 (1.09) | 4.00 (4.00-4.00) | 23.9 (0) | 1.00 (0) |
| | | CV % | 41.0 | 45.6 | 0.0 | 0.0 | 0.0 |
| | 13 | n | 4 | 4 | 4 | 4 | 4 |
| | | Mean (SD) | 50.2 (21.9) | 3.47 (1.38) | 4.00 (3.00-8.00) | 23.6 (0) | 1.41 (0.287) |
| | | CV % | 43.7 | 39.8 | 46.7 | 0.0 | 20.4 |

**Median and range are presented for Tmax

Similar dose dependent increases were noted in repeated daily dosing of Compound A from 10 µg (median Cmax 405 µg/m/L to 100 µg (median Cmax 1054 µg/mL). The pharmacodynamic marker, FGF19 continues to rise with increasing Compound A doses beyond 100 µg in the above study. The 30 µg/day dose resulted in FGF19 elevations consistent with pharmacological activity in NASH.

Results from this clinical study also showed that when Compound A was taken with a high-fat meal, median Tmax was delayed from 4 h to 9 h, and mean Compound A Cmax and AUCinf increased by approximately 60% compared to the fasted state. Individual Compound A fed vs. fasted exposure ratios ranged from 1.17 to 2.27-fold for Cmax and from 1.24 to 1.94-fold for AUCinf. To avoid variability in drug exposure, it is recommended that throughout the treatment period, patients will be directed to take study drug at home with 240 mL (8 ounces) of water in the morning in a fasting state, at least 30 min prior to the first beverage apart from water and 60 min prior to first meal of the day, preferably at the same time of the day.

No safety concerns were identified in single dose studies up to 3000 µg Compound A. In repeated daily administration doses up to and including 60 µg Compound A were well tolerated. At 100 µg Compound A, elevation of transaminases (ALT and AST) occurred in 3 subjects, one with ALT>ULN, one with ALT>3×ULN and one with ALT>5× ULN. Elevations of AST were less marked and no elevation in ALP or bilirubin was noted in any subject. Elevated ALT resolved to within normal levels within 14 days and without intervention.

No significant findings in physical exam, vital signs or ECGs have been related to Compound A; no adverse events related to itch, a common adverse event for bile acid-derived FXR agonists, have been observed in this clinical study.

The data from this clinical trial as well as preclinical evidence presented above show that Compound A at daily doses of 10 µg to 90 µg to be safe and pharmacological active for treatment of liver disease, e.g NASH. Furthermore, FGF19 continues to rise with increasing Compound A doses even beyond 100 µg, e.g. at 120 µg.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

We claim:

1. A method for treating a chronic liver disease or disorder mediated by Farnesoid X receptor (FXR), comprising administering to a subject in need thereof, a compound of Formula (I)

(I)

or a stereoisomer, an enantiomer, a pharmaceutically acceptable salt thereof, an amino acid conjugate, or an acyl glucuronide conjugate thereof, at a dose in a range of about 3 µg to about 120 µg;

wherein said amino acid conjugate or acyl glucuronide conjugate is selected from:

2-({2-[(1R,3R,5S)-3-({5-cyclopropyl-3-[2-(trifluoromethoxy)phenyl]-1,2-oxazol-4-yl}methoxy)-8-azabicyclo[3.2.1]octan-8-yl]-4-fluoro-1,3-benzothiazol-6-yl}formamido)acetic acid;

2-({2-[(1R,3R,5S)-3-({5-cyclopropyl-3-[2-(trifluoromethoxy)phenyl]-1,2-oxazol-4-yl}methoxy)-8-azabicyclo[3.2.1]octan-8-yl]-4-fluoro-1,3-benzothiazol-6-yl}formamido)ethane-1-sulfonic acid; and (2S,3S,4S,5R,6S)-6-((2-((1R,3S,5S)-3-((5-cyclopropyl-3-(2-(trifluoromethoxy)phenyl)isoxazol-4-yl)methoxy)-8-azabicyclo[3.2.1]octan-8-yl)-4-fluorobenzo[d]thiazole-6-carbonyl)oxy)-3,4,5-trihydroxytetrahydro-2H-pyran-2-carboxylic acid.

2. The method according to claim 1, wherein the chronic liver disease or disorder mediated by FXR is non-alcoholic fatty liver disease (NAFLD).

3. The method according to claim 1, wherein the chronic liver disease or disorder mediated by FXR is non-alcoholic steatohepatitis (NASH).

4. The method according to claim 1, comprising administering 2-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]-4-fluoro-1,3-benzothiazole-6-carboxylic acid in a free form.

5. The method according to claim 1, comprising administering the amino acid conjugate 2-({2-[(1R,3R,5S)-3-({5-cyclopropyl-3-[2-(trifluoromethoxy)phenyl]-1,2-oxazol-4-yl}methoxy)-8-azabicyclo[3.2.1]octan-8-yl]-4-fluoro-1,3-benzothiazol-6-yl}formamido)acetic acid.

6. The method according to claim 1, comprising administering the amino acid conjugate 2-({2-[(1R,3R,5S)-3-({5-cyclopropyl-3-[2-(trifluoromethoxy)phenyl]-1,2-oxazol-4-yl}methoxy)-8-azabicyclo[3.2.1]octan-8-yl]-4-fluoro-1,3-benzothiazol-6-yl}formamido)ethane-1-sulfonic acid.

7. The method according to claim 1, comprising administering the acyl glucuronide conjugate (2S,3S,4S,5R,6S)-6-((2-((1R,3S,5S)-3-((5-cyclopropyl-3-(2-(trifluoromethoxy)phenyl)isoxazol-4-yl)methoxy)-8-azabicyclo[3.2.1]octan-8-yl)-4-fluorobenzo[d]thiazole-6-carbonyl)oxy)-3,4,5-trihydroxytetrahydro-2H-pyran-2-carboxylic acid.

8. The method according to claim 1, comprising administering about 10 µg, about 30 µg, about 60 µg, about 90 µg or about 120 µg of 2-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]-4-fluoro-1,3-benzothiazole-6-carboxylic acid, or a pharmaceutically acceptable salt thereof, up to a maximum total dose of about 120 µg per day.

9. The method according to claim 1, wherein the dose is a daily dose.

10. The method according to claim 1, wherein the dose is a twice daily dose.

11. The method according to claim 1, wherein the dose is once every two days.

12. The method according to claim 1, comprising administering about 30 µg to about 90 µg of 2-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]-4-fluoro-1,3-benzothiazole-6-carboxylic acid, or a pharmaceutically acceptable salt thereof.

13. The method according to claim 1, comprising administering about 60 µg of 2-[(1R,3r,5S)-3-({5-cyclopropyl-3-[2-(trifluoromethoxy)phenyl]-1,2-oxazol-4-yl}methoxy)-8- azabicyclo[3.2.1]octan-8-yl]-4-fluoro-1,3-benzothiazole-6-carboxylic acid, or a pharmaceutically acceptable salt thereof.

14. The method according to claim 1, comprising administering about 90 μg of 2-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]-4-fluoro-1,3-benzothiazole-6-carboxylic acid, or a pharmaceutically acceptable salt thereof.

15. The method according to claim 1, comprising administering about 120 μg of 2-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]-4-fluoro-1,3-benzothiazole-6-carboxylic acid, or a pharmaceutically acceptable salt thereof.

16. The method according to claim 1, comprising administering about 60 μg to about 120 μg of 2-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]-4-fluoro-1,3-benzothiazole-6-carboxylic acid, or a pharmaceutically acceptable salt thereof.

17. The method according to claim 1, comprising administering said compound of Formula (I) or a stereoisomer, enantiomer or pharmaceutically acceptable salt, thereof, at a dose of about 10 μg to about 120 μg.

18. A method for treating non-alcoholic fatty liver disease, comprising administering about 10 μg to about 120 μg of 2-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]-4-fluoro-1,3-benzothiazole-6-carboxylic acid, or a pharmaceutically acceptable salt thereof, to a subject in need thereof.

19. The method of claim 18, wherein said non-alcoholic fatty liver disease is non-alcoholic steatohepatitis.

20. The method according to claim 18, comprising administering about 60 μg of 2-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]-4-fluoro-1,3-benzothiazole-6-carboxylic acid.

21. The method according to claim 18, comprising administering about 90 μg of 2-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]-4-fluoro-1,3-benzothiazole-6-carboxylic acid.

22. The method according to claim 18, comprising administering about 120 μg of 2-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]-4-fluoro-1,3-benzothiazole-6-carboxylic acid.

23. The method according to claim 18, comprising administering once a day about 60 μg of 2-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]-4-fluoro-1,3-benzothiazole-6-carboxylic acid.

24. The method according to claim 18, comprising administering once a day about 90 μg of 2-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]-4-fluoro-1,3-benzothiazole-6-carboxylic acid.

25. The method according to claim 18, comprising administering once a day about 120 μg of 2-[(1R,3r,5S)-3-({5-cyclopropyl-3-[2-(trifluoromethoxy)phenyl]-1,2-oxazol-4-yl}methoxy)-8-azabicyclo[3.2.1]octan-8-yl]-4-fluoro-1,3-benzothiazole-6-carboxylic acid.

* * * * *